US010669354B2

(12) United States Patent
Guarise et al.

(10) Patent No.: US 10,669,354 B2
(45) Date of Patent: Jun. 2, 2020

(54) PROCESS FOR THE PRODUCTION OF HIGH-PURITY SULFATED HA

(71) Applicant: FIDIA FARMACEUTICI S.P.A., Abano Terme (PD) (IT)

(72) Inventors: Cristian Guarise, Abano Terme (IT); Mauro Pavan, Abano Terme (IT)

(73) Assignee: FIDIA FARMACEUTICI S.P.A., Abano Terme (PD) (IT)

(*) Notice: Subject to any disclaimer, the term of this patent is extended or adjusted under 35 U.S.C. 154(b) by 25 days.

(21) Appl. No.: 15/776,225

(22) PCT Filed: Nov. 15, 2016

(86) PCT No.: PCT/IB2016/056868
§ 371 (c)(1),
(2) Date: May 15, 2018

(87) PCT Pub. No.: WO2017/085622
PCT Pub. Date: May 26, 2017

(65) Prior Publication Data
US 2019/0263940 A1   Aug. 29, 2019

(30) Foreign Application Priority Data
Nov. 16, 2015  (IT) .............................. UB2015A5623

(51) Int. Cl.
*C08B 37/08* (2006.01)
*A61K 31/737* (2006.01)

(52) U.S. Cl.
CPC ........ *C08B 37/0072* (2013.01); *A61K 31/737* (2013.01)

(58) Field of Classification Search
CPC ............ C08B 37/0072; C08B 37/0075; C08B 37/0069
See application file for complete search history.

(56) References Cited

U.S. PATENT DOCUMENTS

| 5,874,548 A * | 2/1999 | Flitsch ..................... C07H 3/04 536/1.11 |
| 2013/0209531 A1* | 8/2013 | Prestwich .............. A61K 45/06 424/401 |

FOREIGN PATENT DOCUMENTS

| WO | WO 95/25751 A1 | 9/1995 |
| WO | WO 2010/130468 A1 | 11/2010 |

OTHER PUBLICATIONS

International Search Report, issued in PCT/IB2016/056868, dated Feb. 9, 2017.
Written Opinion of the International Searching Authority, issued in PCT/IB2016/056868, dated Feb. 9, 2017.

\* cited by examiner

*Primary Examiner* — Pancham Bakshi
(74) *Attorney, Agent, or Firm* — Birch, Stewart, Kolasch & Birch, LLP

(57) ABSTRACT

The present invention relates to an improved process for the production of sulfated hyaluronic acid (HA), sulfated HA-derivatives and/or mixtures thereof, having a high purity and a sulfation degree ranging from 1 to 3, which comprises the following steps: a) solubilization of HA-Na or HA-derivative-Na, in an aprotic solvent in the presence of an organic sulfonic acid; b) sulfation of the solution obtained by the addition of an excess of sulfating agents; c) precipitation in ethanol until a precipitate is obtained; d) solubilization of the precipitate thus obtained in a mixture of water and the aprotic solvent used in step a), in the presence of an excess of NaCl, with a pH adjustment within a range of 3 to 4; e) further precipitation with ethanol until a powder is obtained; f) washings of the powder coming from step c) and drying the product thus obtained under vacuum. The present invention also relates to sulfated HA, sulfated HA derivatives and/or mixtures thereof, having a high purity and sulfation degree ranging from 1 to 3, thus prepared, and the relative pharmaceutical mixtures.

19 Claims, No Drawings

PROCESS FOR THE PRODUCTION OF HIGH-PURITY SULFATED HA

The present invention relates to an improved process for the production of high-purity sulfated HA.

The possibility has long been known of chemically derivatizing hyaluronic acid (HA) in order to obtain structures that maintain the physico-chemical properties of the starting molecule, acquiring new specific features. In short, HA is a hetero-polysaccharide consisting of alternating residues of D-glucuronic acid and N-acetyl-D-glucosamine, with a linear chain, having a molecular weight that can range from 50,000 to $13 \times 10^6$ Da, depending on the source from which it is obtained and also the preparation methods used.

Hyaluronic acid is virtually ubiquitous in the human body, in which it plays an important role above all, but not only, as a mechanical support of cells of numerous tissues, such as the skin, tendons, muscles and cartilage. The interactions of HA with its membrane receptor CD44 and with opiate receptors are also known.

Due to its chemical nature, HA has numerous derivatizable functional groups. In this case, among the various possible modifications known to skilled persons in the field, the modification of interest for the present invention is sulfation, i.e. enrichment with $—SO_3$ groups. This derivatization can take place with respect to both the numerous —OH groups available (O-sulfation) and also the amine group of the N-acetyl-D-glucosamine residue, after deacetylation of the same (N-sulfation) (EP 702699; EP 940410; EP 971961; EP 889055). The different derivatization makes the molecules suitable for various uses; N-sulfated derivatives are, in fact, particularly useful for the production of medical devices. The properties of the sulfated product also depend on the sulfation degree, expressed as the number of $—SO_3$ groups present per disaccharide unit.

The hyaluronic acid sulfated derivative of interest for the purposes of the present invention is the O-sulfated derivative, which is simply indicated in the present patent application as HAS, and which is capable of easily passing through the skin barrier, facilitating the passage of substances associated with the same. These characteristics make it an excellent vehicle for the skin absorption of pharmacologically and biologically active molecules. Sulfation also gives hyaluronic acid HA anticoagulant heparin-like properties that have been exploited, for example, in the coating of vascular stents.

It has also been recently discovered and demonstrated that HAS has actual pharmacological properties: it is a powerful anti-inflammatory agent, that exerts its action by means of an effective modulation of the activity of numerous cytokines, both pro- and anti-inflammatory. Thanks to this, HAS can be applied in the therapy of numerous diseases mediated by alteration of the cytokine levels (rheumatoid arthritis, asthma, systemic and cutaneous autoimmune diseases, viral infections, atopic dermatitis, eczema, vitiligo, lymphomas, etc.) (WO2010130468; WO2010130466).

The processes currently known for the production of HA are processes characterized by relatively limited production yields and compulsory purification steps that strictly require a dialysis phase.

A therapeutic use of HA and/or its sulfated derivatives, which is potentially so vast, therefore also creates the problem of a productive nature, which the present invention proposes to solve, by finding a process for the production of sulfated HA and/or its sulfated derivatives, which is more rapid, less consuming in terms of time and raw materials, and is above all particularly effective with respect to both process yield and purity of the end-product.

OBJECT OF THE INVENTION

An object of the present invention therefore relates to an improved process for the production of sulfated hyaluronic acid (HA), sulfated HA-derivatives and/or mixtures thereof, having a high purity and a sulfation degree ranging from 1 to 3, wherein said process comprises the following steps:

a) solubilization of HA-Na or HA derivative-Na, in an aprotic solvent preferably selected from dimethyl sulfoxide (DMSO), N,N-dimethylformamide (DMF) or N-methylpyrrolidone (NMP), more preferably DMSO, in the presence of an organic sulfonic acid, preferably methanesulfonic acid, in a quantity ranging from 4.5 to 5.5 mol/mol equivalents with respect to the repetitive disaccharide unit of HA or of HA derivative;

b) sulfation of the solution obtained at the end of step a) by the addition of an excess of $SO_3$-pyridine, $SO_3$-trimethylamine, or other sulfating agents, preferably $SO_3$-pyridine;

c) precipitation in ethanol, preferably absolute ethanol, until a precipitate is obtained;

d) solubilization of the precipitate thus obtained in a mixture of water and the aprotic solvent used in step a), in the presence of an excess of NaCl, said excess calculated with respect to the residual sulfate groups, with a pH adjustment within a range of 3 to 4;

e) further precipitation with ethanol, preferably absolute ethanol, until a powder is obtained;

f) washings of the powder coming from step e) and drying the product thus obtained under vacuum.

The washings provided in step f) of the process according to the present invention can be effected on the product obtained in step e) as follows:

f') elimination of the solvent by washing the precipitate three times with ethanol/water in a ratio of 8:2;

f") elimination of the pyridine residues by successive washings with ethanol/NaOH 0.1 M 8:2; ethanol/HCl 8:2; ethanol/water 8:2 and finally with absolute ethanol.

A further object of the present invention relates to sulfated hyaluronic acid (HA) or sulfated derivatives of HA, and/or mixtures thereof, with a sulfation degree ranging from 1 to 3 and with a degree of purity higher than 98%, that can be obtained with the process according to the present invention.

An object of the present invention also relates to pharmaceutical compositions comprising sulfated hyaluronic acid or sulfated HA derivatives, and/or mixtures thereof, with a sulfation degree ranging from 1 to 3 and with a degree of purity higher than 98%, that can be obtained with the process according to the present invention, in the presence of pharmaceutically acceptable additives.

The new improved process for the production of sulfated HA with a degree ranging from 1 to 3 according to the present invention, has the main advantage of being particularly rapid, less consuming in terms of time and raw materials, and above all of being surprisingly more effective than processes for the production of sulfated HA currently known, in terms of both process yield and purity of the end-product.

The sulfation process of hyaluronic acid and/or its derivatives according to the present invention, through the elimination of some steps (mainly a dialysis step) considered necessary in all processes of the state of the art, and with the insertion of essential technical modifications, surprisingly allows a purer end-product to be obtained with very high yields.

A particularly advantageous aspect of the process according to the present invention is, in fact, the formation of an extremely fine and pure precipitate at the end of the precipitation phase e), which has allowed one of the main steps of the known processes to be eliminated, and specifically the dialysis step. The purity of the end-product also affects its specific characteristics; in the formulation phase of pharmaceutical compositions, for example, the risk of interaction between the "active principle" (sulfated HA, or HA-derivative) obtained according to the present invention and the other components of the formulation, whether they be excipients or other pharmacologically and/or biologically active substances, is minimized. The process according to the present invention is also characterized by extremely high yields, practically quantitative, absolutely unexpected according to the teachings of the prior art.

The starting hyaluronic acid used in the process according to the present invention can derive from any source, for example, from extraction from rooster combs (EP138572), fermentation, as known to skilled persons in the field, or biosynthesis (from *Bacillus*, WO2012032154), and has an average molecular weight ranging between 100,000 and 250,000 Da, preferably between 180,000 and 230,000 Da, or between 500,000 and 750,000 Da, preferably from 700,000 to 730,000 Da.

It should be pointed out that average Molecular Weight (MW) refers to the weight average MW calculated with the "intrinsic viscosity" method (Terbojevich et al., Carbohydr. Res., 1986, 363-377).

In the present patent application, which enhances the preparation process of sulfated HA with a degree ranging from 1 to 3, the term sulfation degree refers to the number of —$SO_3$ groups per repetitive disaccharide unit, and more specifically:

degree 1 sulfation comprises from 0.5 to 1.5 sulfate groups;

degree 2 sulfation comprises from 1.5 to 2.5 sulfate groups;

degree 3 sulfation comprises from 2.5 to 3.5 sulfate groups.

The process, object of the present invention, allows not only sulfated HA to be successfully produced, but also sulfated derivatives of hyaluronic acid, i.e. starting from more complex molecules obtained by chemically modifying the starting HA, such as:

amides of HA with amines of the aliphatic, arylaliphatic, cycloaliphatic, aromatic, cyclic and heterocyclic series, with an amidation percentage ranging from 0.1 to 50%, whereas the remaining percentage of HA not subjected to amidation can be salified with organic and/or inorganic bases (HYADD®—EP 1095064 B1);

esters of HA with alcohols of the aliphatic, arylaliphatic, cycloaliphatic, aromatic, cyclic and heterocyclic series, with an esterification percentage that can range, depending on the type and chain length of the alcohol used, preferably between 50 and 100%, whereas the remaining percentage of non-esterified HA can be salified with organic and/or inorganic bases (HYAFF®—EP 216453 B1);

internal esters of HA with an esterification percentage not exceeding 20%, preferably with an esterification of 0.05 to 10%, whereas the remaining percentage of non-esterified HA can be salified with organic and/or inorganic bases (ACP®—EP 341745 B1).

The sulfated hyaluronic acid thus obtained can be used as such, but it can also be used as starting compound for further derivatizations. It can be bound, for example, to photoreactive molecules through a spacer, or to other chemical entities for carrying out reactions known in the state of the art (for example click-chemistry reactions).

DETAILED DESCRIPTION OF THE INVENTION

Sulfation processes known in the state of the art generally comprise the following steps:

dissolution of HA in salt form (preferably tetrabutylammonium—TBA), in an aprotic solvent (DMSO, DMF, etc.). Even if dissolution of HA is generally indicated, in this first step, in reality, a dissolution is not obtained but more appropriately a suspension as HA is not soluble in aprotic solvent and it is specifically to make it more easily suspendable that HA is derivatized to ammonium salt;

sulfation by the addition of an excess of $SO_3$-pyridine, $SO_3$-trimethylamine, or other equivalent agents known to skilled persons in the field;

first precipitation with organic solvent;

centrifugation to isolate the precipitate;

dissolution of the precipitate thus obtained;

second precipitation of the "pure" product and dialysis to eliminate solvents and other residues.

In the methods of the state of the art, the "dissolution of the precipitate" and "second precipitation" steps are repeated various times to eliminate at least the excesses of solvent and reagents.

It is evident that the process according to the present invention differs considerably from the processes of the state of the art, in particular in some of the steps, schematized hereunder, bearing in mind, first of all, that the starting material in the case of the process according to the present invention is exclusively sodium salt, whether it be the case of HA as such, or one of the derivatives indicated above. If the starting polymer is HA, it will have an average starting MW ranging between 100,000 and 250,000 Da, in particular between 180,000 and 230,000 Da or between 500,000 and 750,000 Da, in particular from 700,000 to 730,000 Da. In the state of the art, although sodium salt is a possibility taken into consideration, regardless of the MW used, the starting material is generally tetrabutylammonium salt, i.e. Hyaluronic Acid TBA (tetrabutylammonium) salt, which must be previously synthesized; this implies a further preliminary production step.

The steps that characterize the process according to the present invention are steps a), c)-e) of the following procedure:

a) solubilization of HA-Na (or HA-derivative-Na), in an aprotic solvent with the addition of an organic sulfonic acid, preferably methanesulfonic acid; this addition allows an actual limpid solution to be obtained, which, at 600 nm, has an absorbance value ≤0.04 AU, which is a standard reference value for defining the limpidity; the total solubilization of HA ensures the quantitative sulfation of the polymer, in the predetermined degree. This use of methanesulfonic acid or other organic sulfonic acids, has never been described for these purposes in the state of the art;

the aprotic solvent is preferably selected from DMSO (dimethylsulfoxide), DMF (N,N-dimethyl-formamide) or NMP (N-methylpyrrolidone), and is even more preferably DMSO;

the quantity of methanesulfonic acid to be used ranges from 4.5 to 5.5 mol/mol equivalents, and is preferably equal to 5 mol/mol equivalents with respect to the repetitive disaccharide unit of HA. Lower values do not allow solubilization whereas higher values allow solubilization but, in the final precipitation phase, a drastic drop in the yield (<60%) has been observed (as indicated in Table 1);

the solubilization is carried out for a time ranging from 20 to 28 hours, at a temperature T ranging from 20 to 30° C., preferably for 24 hours at 25° C., until a limpid solution is obtained;

b) sulfation: this step is carried out according to the known art, by the addition of an excess of $SO_3$-pyridine, $SO_3$-trimethylamine, or other agents known to skilled persons in the field, preferably $SO_3$-pyridine (complex of pyridine sulfur trioxide);

c) first precipitation in ethanol, preferably absolute ethanol, until a brown rubbery precipitate is obtained;

d) solubilization of the precipitate thus obtained in water (known art), in the presence of NaCl and the same aprotic solvent in which the raw material has been solubilized, with a pH adjustment within a range of 3 to 4, preferably from 3.3 to 3.5. The quantity of NaCl added must be in absolute excess to ensure that all the residual sulfate groups are in the form of sodium salt (see Table 2);

e) second precipitation with ethanol, preferably absolute ethanol, whereby an extremely fine and pure precipitate is obtained, with only one passage, which does not require dialysis, and which can pass directly to the subsequent steps;

f) repeated washings and drying of the product thus obtained under vacuum.

The washings provided in step f) of the process according to the present invention can be effected on the product obtained in step e) as follows:

f') elimination of the solvent by washing the precipitate three times with ethanol/water in a ratio of 8:2;

f") elimination of the pyridine residues by consecutive washings with ethanol/NaOH 0.1 M 8:2; ethanol/HCl 8:2; ethanol/water 8:2 and finally with absolute ethanol. The washing with Ethanol/NaOH 0.1 M 8:2 is particularly important in this step as it allows the almost total elimination of the pyridine, giving the resulting powder an extremely high purity, always >98% (Table 3 indicates the tests effected in this sense).

The vacuum drying is carried out according to the known art.

The process according to the present invention is characterized by extremely high yields: the process, in fact, allows yields ≥98% to be obtained; the combination of steps that characterize the process according to the present invention allows all the HA used to be practically quantitatively sulfated. This result is absolutely surprising as the known processes according to the state of the art describe much lower yields:

EP 889055, Shiseido, Example 2: 1.2 g of HAS are obtained from 2 g of starting HA (yield 50%; sulfation degree calculated 20%);

EP 702699, Fidia, Example 1: yield 62% approximately for sulfation degree 3;

WO 2010130446, Fidia, Example 2: yield described within the range of 86-88% for HAS degree 3 (9.7 g of HAS 3 are obtained from 10 g of HA-TBA).

The process according to the present invention is also characterized by the production of a product having a purity higher than 98%: the sulfated product obtained is an extremely fine powder, with negligible residues of pyridine and organic solvent, which consequently does not require a dialysis step, unlike what is known in the state of the art:

EP 889055, Shiseido, Example 2: "overnight" dialysis against 3 litres of distilled water, to be substituted 3 times;

EP 702699, Example 1 and WO 2010/130446, Example 2: duration of the dialysis not specified, but conducted until the elimination of the reaction residues.

The elimination of the dialysis step is extremely important in industrial terms, as it represents a significant saving (fewer steps, shorter waiting times, fewer disposals). The absence of any dialysis step is consequently an essential aspect of the process according to the present invention.

The production of a high-purity product is therefore important not only because it allows an onerous industrial step to be eliminated, but also, in an absolute sense, because an end-product that can be used as such coming from the production process, without any further precautions with respect to the degree of purity, enormously simplifies the work of a technical formulator; by using sulfated HA (or HA derivatives) according to the present invention, in fact, he can prepare any pharmaceutical form without any type of risk linked to impurities, normally present at the end of a chemical synthesis.

It should be remembered, in fact, that for some pharmaceutical forms, products having a high degree of purity, but not absolute, i.e. so-called "cosmetic degree", are sufficient; these are generally pharmaceutical forms to be used, for example, on undamaged skin, in functional foods or in food supplements, etc.

Other pharmaceutical forms, on the other hand, require products with a "pharmaceutical degree" of purity: i.e. the products must be extremely pure, to allow them to be also used in specific pharmaceutical forms, such as, for example, injections (intradermal, intramuscular, intravenous, intraocular) or in particular regions (skin damaged by ulcers, herpes infections, vascular disorders, mucose, etc.).

These particularly advantageous technical results are due to the combination of various essential features of the process according to the present invention and specifically:

the presence of an organic sulfonic acid, preferably methanesulfonic acid, in the solubilization step of HA-Na (or HA-derivative-Na) in the preselected aprotic solvent;

the solubilization of the precipitate in water, in the presence of an excess of NaCl and aprotic solvent used initially; and adjustment of the pH within a very narrow range of values, before the final precipitation with ethanol.

The pH values are fundamental: the data indicated in Table 2 below show that even minimum variations with respect to the range claimed, lead to the formation of a "muddy" precipitate that inevitably requires several dialysis steps before being able to be washed and dried with standard techniques.

This is not an adjustment described or envisaged on the basis of the known art, as the precipitation is described in the prior art at neutral pH (EP 8890559, WO 2010/130446) or definitely basic (EP 702699). Consequently it was completely unpredictable that stabilization at typically acid pH values could lead to the surprising results of the process according to the present invention.

The process according to the present invention therefore not only remarkably improves the process yield and purity of the product, but also allows some process steps to be eliminated with respect to the known processes, consequently also making it industrially more convenient.

These results are totally unpredictable and surprising in view of the contents of the prior art.

TABLE 1

Evaluation of the effect of methanesulfonic acid on the solubilization of HA-Na in DMSO (T 24° C.; Time: 24 hours)

| | | | | | | |
|---|---|---|---|---|---|---|
| HA-Na 200 kDa (g) | 1.00 g | 1.00 g | 1.00 g | 1.00 g | 1.00 g | 1.00 g |
| DMSO (ml) | 55 ml | 55 ml | 55 ml | 55 ml | 55 ml | 55 ml |
| Methanesulfonic acid | 0 | 0.16 ml | 0.48 ml | 0.64 ml | 0.73 ml | 0.89 ml |
| Equivalents. (mol/mol) vs HA disaccharide unit | 0 | 1 | 3 | 4 | 4.5 | 5.5 |
| Absorbance 600 nm (*) | 0.65 | 0.41 | 0.15 | 0.09 | 0.04 | 0.01 |
| Solubilization | Non-homogeneous suspension | Non-homogeneous suspension | Non-homogeneous suspension | Non-homogeneous suspension | Limpid colourless solution | Limpid colourless solution |

(*) Measurement effected with a UV/Vis spectrophotometer against DMSO (blank); it expresses the degree of limpidity: a solution is limpid when it has absorbance values at 600 nm ≤ 0.04 AU.

The importance of the addition of methanesulfonic acid is evident. Further tests showed that by using higher quantities of methanesulfonic acid (6 and 6.5 mol/mol equivalents), the solubilization of HA-Na is complete, but in the final precipitation phase, there is a drastic reduction in the yield, which is lower than the yields of processes according to the known art, and in addition, the precipitate obtained has a degree of purity lower than 90%.

TABLE 2

Characteristics of the precipitate in relation to the presence of NaCl, DMSO and to the adjustment of the pH before the 2$^{nd}$ precipitation with ethanol.

| | 1 | 2 | 3 | 4 | 5 | 6 | 7 |
|---|---|---|---|---|---|---|---|
| HAS3 (from first precipitation) as in Example 1 Solubilization in: | Brown rubbery precipitate | Brown rubbery precipitate | Brown rubbery precipitate | Brown rubbery precipitate | Brown rubbery precipitate | Brown rubbery precipitate | Brown rubbery precipitate |
| H$_2$O (ml) | 56 ml | 56 ml | 32 ml | 32 ml | 32 m | 32 ml | 32 ml |
| NaCl (g) | 1.3 g | 1.3 g | 0 g | 1.3 g | 1.3 g | 1.3 g | 1.3 g |
| DMSO (ml) | 0 ml | 0 ml | 24 ml | 24 ml | 24 ml | 24 ml | 24 ml |
| pH | pH 1.9 | pH 3.4 | pH 3.5 | pH 4.5 | pH 7 | pH 1.9 | pH 3.5 |
| Appearance of precipitate (after 2$^{nd}$ precipitation with ethanol | Yellowish rubbery precipitate | Milky mixture | Milky mixture | Yellowish rubbery precipitate | Yellowish rubbery precipitate | White rubbery precipitate | Very fine yellowish-white powder |

The pH of the solutions indicated in columns 2-5 and 7 were adjusted with NaOH 3M. The pH indicated in columns 1 and 6 is that obtained in the reaction environment.

The combination of water, organic solvent and correct pH value produces the desired effect: only when conditions of the presence of DMSO, NaCl and pH adjustment are verified according to the object of the present invention, is the precipitate obtained in the form of a very fine, pure powder, with high yields.

TABLE 3 influence of the Ethanol/NaOH mixture in the washing steps

| HAS3 after 2$^{nd}$ precipitation (Example 1) | Very fine yellowish-white powder | Very fine yellowish-white powder | Very fine yellowish-white powder | Very fine yellowish-white powder |
|---|---|---|---|---|
| Washings (nr.): | | | | |
| Ethanol/Water (8:2) | nr. 6 × 15' | nr. 6 × 15' | nr. 3 × 15' | nr. 3 × 15' |
| Ethanol/NaOH 0.1M (8:2) | 0 | 0 | nr. 4 × 15' | nr. 3 × 15' |
| Ethanol/HCl 0.1M (8:2) | nr. 2 × 15' | 0 | 0 | nr. 2 × 15' |
| Ethanol/Water (8:2) | nr. 2 × 15' | nr. 4 × 15' | nr. 4 × 15' | nr. 2 × 15' |
| Ethanol | nr. 2 × 15' | nr. 2 × 15' | nr. 2 × 15' | nr. 2 × 15' |

TABLE 3-continued influence of the Ethanol/NaOH mixture in the washing steps

| HAS3 after 2$^{nd}$ precipitation (Example 1) | Very fine yellowish-white powder | Very fine yellowish-white powder | Very fine yellowish-white powder | Very fine yellowish-white powder |
|---|---|---|---|---|
| Pyridine content after drying (% w/w) | 0.47% | 0.56% | 0.016% | 0.014% |

The addition of the mixture of Ethanol/NaOH 0.1 M 8:2 in the washing steps allows the residual pyridine content in the end-product to be drastically reduced (≤0.02% w/w), even more so when it is used before the Ethanol/HCl 0.1 M mixture. The latter, on the other hand, if used alone, does not allow an adequate elimination of the pyridine.

In the following examples, as in the above tables, the sulfation degree was determined by means of ICP-OES analysis (atomic emission spectroscopy analysis with plasma source), known to skilled persons in the field; the molar DS is calculated with this technique, which expresses the quantity of S bound to HA and therefore the substitution degree per disaccharide unit (Sulfur Standard for ICP "18021 Sigma-Aldrich TraceCERT®). The average MW per repetitive unit of the HAS sample is calculated from the molar DS and subsequently the content of moles which, when compared to those of the starting HA, express the % yield (Macromolecules, 2005, 38, 4647-4654).

The impurities (pyridine and DMSO) were analyzed by means of Gas Chromatography with direct injection effected on the end-product, calculating its total ratio (w/w %) with respect to the HAS produced, according to the known art (European Pharmacopoeia 8.0, Par 5.4: Residual Solvent).

As already mentioned, the sulfated hyaluronic acid (or its derivatives) obtained according to the present invention is not only economically convenient from an industrial point of view, but above all it has a high degree of purity; this means that it can be used, as such or suitably combined with other substances, in the preparation of pharmaceutical compositions destined for any route of administration, from cutaneous to intravenous, in the treatment of a wide variety of diseases, in which the therapeutic role of sulfated HA has been carefully examined by scientific studies and is therefore well known in the state of the art.

In this respect, it should be remembered that sulfated HA can be used in:
  diseases related to immune system defects;
  diseases related to an increase in or activation of inflammatory cytokines, such as, for example, TNF, that can arise both systemically (osteoarthritis, rheumatoid arthritis, asthma, vascular disease, vasculitis, deep vein thrombosis, scleroderma, etc.) and also in the skin (non-specific dermatitis, atopic dermatitis, seborrheic dermatitis, urticaria, photodermatitis, eczema, skin and/or mucosal irritations, aphthous stomatitis, fissures, etc.) or particular regions (interstitial cystitis etc.);
  diseases related to dermal-cutaneous manifestations of damage to the vascular endothelium, such as traumas, surface and/or deep vascular bleeding, oedema, hematoma, clot debridement (fibrinolytic effect), etc.;
  autoimmune disorders, comprising rheumatoid arthritis, Crohn's disease and all chronic inflammatory bowel diseases, asthma, diabetes mellitus, multiple sclerosis and demyelinating diseases, astrocytosis, astrogliosis, organ rejection following transplantation, etc. In addition, autoimmune diseases with dermal-cutaneous manifestations include psoriasis, lupus erythematosus and/or Discoid, dermatitis, eczema, etc;
  viral diseases such as HIV infections, Herpes simplex labialis or genitalis, Cytomegalovirus, vesicular stomatitis virus. For these diseases, sulfated HAS degree 1 or 3 has proved to be particularly active. Sulfated HA also has extremely high hydrating properties, thanks to the sulfate groups that allow it to pass through the skin barrier much more easily than the starting molecule and accumulate in the surface layers of the skin. These properties can be applied in any form of skin disease characterized by dryness, lichenification, roughness, itching, redness, inflammation and surface desquamation.

Thanks to its remarkable skin penetration, sulfated HA acts as an excellent promoter of dermal absorption of molecules which, alone, can not cross the skin barrier. In this way, the molecules can reach the dermis and exert their effect. These molecules can be drugs (for example, steroidal and non-steroidal anti-inflammatory agents, chemotherapeutics for topical use, antibiotics, antivirals, anticoagulants and/or fibrinolytics, local anesthetics, anticholinergics, vasodilators, vasoconstrictors), hormones, proteins, enzymes (eg, collagenase, hyaluronidase, protease), extracts of plants, other polymers (for example, chondroitin sulfate, chemically modified derivatives of hyaluronic acid).

The pharmaceutical compositions comprising sulfated hyaluronic acid or sulfated HA derivatives, and/or mixtures thereof, with a sulfation degree ranging from 1 to 3 and with a degree of purity higher than 98%, which can be obtained with the process according to the present invention, in the presence of suitable pharmaceutically acceptable additives, can be used for topic administration (in the form of creams, gels, salves, ointments, films, lotions, medicated and transdermal plasters, etc.), oral administration (in the form of capsules, tablets, powders, granulates, beverages, functional foods, etc.), injectable administration (intradermal, intraarticular, intravenous, intramuscular, etc.), transmucosal administration (rectal, vaginal, buccal), by inhalation and loco-regional administration (for example, intraocular, intravesical).

The pharmaceutical form is obviously selected on the basis of the therapeutic use and application site; regardless of the pharmaceutical form selected, said pharmaceutical compositions can further comprise biologically and/or pharmacologically active substances, both synthetic and of a natural origin, such as drugs, plant extracts, proteins, peptides, vitamins, amino acids, glycosaminoglycans, polymers of a natural, semi-synthetic or synthetic origin; the latter category also includes the hyaluronic acid derivatives obtained by esterification with benzyl alcohol (HYAFF®), by amidation with hexadecyl amide (HYADD®, amidation degree 5%), by internal esterification (ACP®, esterification degree 5%), etc.

Among the possible associations, the following can be mentioned:

HAS degree 1 or 2 according to the present invention associated with hyaluronic acid esterified with benzyl alcohol, with an esterification percentage ranging from 50 to 100%, preferably from 50 to 75%, in the treatment of interstitial cystitis;

HAS degree 1 or 3 associated with natural extracts (*Boswella*), vitamins and urea in the treatment of psoriasis and seborrheic dermatitis.

HAS degree 1 or 2 associated with chondroitin sulfate in the loco-regional treatment of diseases of the urinary system;

HAS degree 1 or 2 and/or with chondroitin sulfate and/or HA for the intra-articular treatment of cartilage damage (from aging, trauma, osteoarthritis).

The present invention is illustrated in greater detail in the following examples.

Example 1

Sulfation of Hyaluronic Acid Sodium Salt (HANa) with MW 200 kDa in DMSO—Sulfation Degree 3

1) 1.00 grams of HANa were suspended in 55 ml of dimethylsulfoxide (DMSO). 0.8 ml of pure methanesulfonic acid were added to this suspension and the mixture was mixed for 24 hours at 25° C.; a limpid colourless solution was thus obtained (Absorbance at 600 nm=0.02 AU). 5.0 g of the complex pyridine sulfur trioxide (Pyridine $SO_3$) were added to this solution, leaving the mixture under stirring for a further 24 hours at 25° C.

2) 90 ml of ethanol were then added to the solution, obtaining a brown-coloured rubbery precipitate. The product thus obtained was separated by filtration, solubilized in 32 ml of water and 1.3 g of NaCl were added. 24 ml of DMSO were finally added and the pH was adjusted to a value equal to 3.4 with NaOH 3M. The derivative thus obtained was precipitated in the form of a very fine powder, by the addition of 90 ml of ethanol. The product thus obtained was separated by filtration, washed 3 times with a solution of Ethanol/water (8/2). In order to eliminate the residual pyridine, the powder was washed 3 times with a solution of Ethanol/NaOH 0.1M (8:2), twice with a solution of Ethanol/HCl 0.1M (8:2), twice with a solution of Ethanol/water (8:2) and finally, twice with pure ethanol. The yellowish-white powder thus obtained was dried in a vacuum pump at 40° C. for 24 hours.

1.70 g of a very fine yellowish-white powder were obtained, which correspond to a yield of 98%, with a purity of 99.4%.

Example 2

Sulfation of Hyaluronic Acid Sodium Salt (HANa) with MW 200 kDa in DMSO—Sulfation Degree 2

1.00 grams of HANa were suspended in 55 ml of dimethylsulfoxide (DMSO). 0.8 ml of pure methanesulfonic acid were added to this suspension and the mixture was mixed for 20 hours at 25° C.; a limpid colourless solution was thus obtained (Absorbance at 600 nm=0.02 AU). 4.0 g of the complex pyridine sulfur trioxide (Pyridine $SO_3$) were added to this solution, leaving the mixture under stirring for a further 22 hours at 23° C.

The same procedure was then carried out according to what is described in Example 1, item 2.

1.51 g of a very fine yellowish-white powder were obtained, which correspond to a yield of 98%, with a purity of 99.2%.

Example 3

Sulfation of Hyaluronic Acid Sodium Salt (HANa) with MW 200 kDa in DMSO—Sulfation Degree 1

1.00 grams of HANa were suspended in 55 ml of dimethylsulfoxide (DMSO). 0.8 ml of pure methanesulfonic acid were added to this suspension and the mixture was mixed for 26 hours at 26° C.; a limpid colourless solution was thus obtained (Absorbance at 600 nm=0.02 AU). 2.4 g of the complex pyridine sulfur trioxide (Pyridine $SO_3$) were added to this solution, leaving the mixture under stirring for a further 27 hours at 27° C.

The same procedure was then carried out according to what is described in Example 1, item 2.

1.26 g of a very fine white powder were obtained, which correspond to a yield of 99%, with a purity of 99.5%.

Example 4

Sulfation of Hyaluronic Acid Sodium Salt (HANa) with MW 700 kDa in DMSO—Sulfation Degree 3

1.00 grams of HANa were suspended in 55 ml of dimethylsulfoxide (DMSO). 0.8 ml of pure methanesulfonic acid were added to this suspension and the mixture was mixed for 20 hours at 28° C.; a limpid colourless solution was thus obtained (Absorbance at 600 nm=0.02 AU). 5.0 g of the complex pyridine sulfur trioxide (Pyridine $SO_3$) were added to this solution, leaving the mixture under stirring for a further 1.5 hours at 29° C.

The same procedure was then carried out according to what is described in Example 1, item 2.

1.75 g of a very fine yellowish-white powder were obtained, which correspond to a yield of 98%, with a purity of 99.1%.

Example 5

Sulfation of Hyaluronic Acid Sodium Salt (HANa) with MW 200 kDa in NMP—Sulfation Degree 3

1.00 grams of HANa were suspended in 55 ml of N-Methyl-Pyrrolidone (NMP). 0.8 ml of pure methanesulfonic acid were added to this suspension and the mixture was mixed for 23 hours at 25° C.; a limpid colourless solution was thus obtained (Absorbance at 600 nm=0.02 AU). 5.0 g of the complex pyridine sulfur trioxide (Pyridine $SO_3$) were added to this solution, leaving the mixture under stirring for a further 20 hours at 24° C.

The same procedure was then carried out according to what is described in Example 1, item 2.

1.67 g of a very fine yellowish-white powder were obtained, which correspond to a yield of 98%, with a purity of 98.9%.

Example 6

Sulfation of Hyaluronic Acid Sodium Salt (HA-Na) with MW 200 kDa in N,N-Dimethylformamide (DMF)—Sulfation Degree 3

1.00 grams of HANa were suspended in 55 ml of N,N-dimethylformamide (DMF). 0.8 ml of pure methanesulfonic acid were added to this suspension and the mixture was mixed for 25 hours at 22° C.; a limpid colourless solution was thus obtained (Absorbance at 600 nm=0.02 AU). 5.0 g of the complex pyridine sulfur trioxide (Pyridine $SO_3$) were added to this solution, leaving the mixture under stirring for a further 25 hours at 22° C.

The same procedure was then carried out according to what is described in Example 1, item 2.

1.73 g of a very fine yellowish-white powder were obtained, which correspond to a yield of 98%, with a purity of 99.1%.

The invention claimed is:

1. An improved process for the production of sulfated hyaluronic acid (HA), sulfated HA-derivatives and/or mixtures thereof, having a high purity and a sulfation degree ranging from 1 to 3, wherein said process comprises the following steps:
   a) solubilization of HA-Na or HA-derivative-Na, in an aprotic solvent, in the presence of an organic sulfonic acid in a quantity ranging from 4.5 to 5.5 mol/mol equivalents with respect to the repetitive disaccharide unit of HA or HA derivative;
   b) sulfation of the solution obtained at the end of step a) by the addition of an excess of $SO_3$-pyridine or $SO_3$-trimethylamine;
   c) precipitation in ethanol, to obtain a precipitate;
   d) solubilization of the precipitate thus obtained in a mixture of water and the aprotic solvent used in step a), in the presence of an excess of NaCl, said excess being calculated with respect to the residual sulfate groups, with a pH adjustment within a range of 3 to 4;
   e) further precipitation with ethanol, to obtain a powder;
   f) washings of the powder coming from step e) and drying the product thus obtained under vacuum.

2. The process according to claim 1, wherein the washings of step f) are the following:
   f') elimination of the solvent by washing the precipitate three times with ethanol/water in a ratio of 8:2;
   f'') elimination of the pyridine residues by successive washings with ethanol/NaOH 0.1 M 8:2; ethanol/HCl 8:2; ethanol/water 8:2 and finally with absolute ethanol.

3. The process according to claim 1, wherein the solubilization step a) is carried out for a time ranging from 20 to 28 hours, at a temperature T ranging from 20 to 30° C.

4. The process according to claim 1, wherein the solubilization step a) is carried in the presence of an organic sulfonic acid which is methanesulfonic acid.

5. The process according to claim 1, wherein in step d), the pH is adjusted within a range of 3.3 to 3.5.

6. The process according to claim 1, wherein the hyaluronic acid of the HA-Na used in step a) has a starting average molecular weight between 100,000 and 250,000 Da or between 500,000 and 750,000 Da.

7. The process according to claim 1, wherein the HA-derivative of the HA-derivative-Na used in step a) is selected from
   amides of HA with amines of the aliphatic, arylaliphatic, cycloaliphatic, aromatic, cyclic and heterocyclic series, with an amidation percentage ranging from 0.1 to 50%;
   esters of HA with alcohols of the aliphatic, arylaliphatic, cycloaliphatic, aromatic, cyclic and heterocyclic series, with an esterification percentage that ranges according to the type and chain length of the alcohol selected; and
   internal esters of HA with an esterification percentage not exceeding 20%;
   the remaining percentage of HA, not subjected to amidation or not esterified, respectively, being salified with organic and/or inorganic bases.

8. The process according to claim 2, wherein the solubilization step a) is carried out for a time ranging from 20 to 28 hours, at a temperature T ranging from 20 to 30° C.

9. The process according to claim 2, wherein the solubilization step a) is carried in the presence of an organic sulfonic acid which is methanesulfonic acid.

10. The process according to claim 3, wherein the solubilization step a) is carried in the presence of an organic sulfonic acid which is methanesulfonic acid.

11. The process according to claim 2, wherein in step d), the pH is adjusted within a range of 3.3 to 3.5.

12. The process according to claim 3, wherein in step d), the pH is adjusted within a range of 3.3 to 3.5.

13. The process according to claim 4, wherein in step d), the pH is adjusted within a range of 3.3 to 3.5.

14. The process according to claim 2, wherein the hyaluronic acid of the HA-Na used in step a) has a starting average molecular weight between 100,000 and 250,000 Da or between 500,000 and 750,000 Da.

15. The process according to claim 3, wherein the hyaluronic acid of the HA-Na used in step a) has a starting average molecular weight between 100,000 and 250,000 Da or between 500,000 and 750,000 Da.

16. The process according to claim 4, wherein the hyaluronic acid of the HA-Na used in step a) has a starting average molecular weight between 100,000 and 250,000 Da or between 500,000 and 750,000 Da.

17. The process according to claim 1, wherein the aprotic solvent of step a) is dimethyl sulfoxide, N,N-dimethylformamide or N-methylpyrrolidone.

18. The process according to claim 3, wherein the solubilization step a) is carried out for a time of 24 hours at a temperature T of 25° C.

19. The process according to claim 1, wherein the HA-derivative of the HA-derivative-Na used in step a) is selected from
   esters of HA with alcohols of the aliphatic, arylaliphatic, cycloaliphatic, aromatic, cyclic and heterocyclic series, with an esterification percentage that ranges between 50 and 100%; and
   internal esters of HA with an esterification percentage between 0.05 and 10%;
   the remaining percentage of HA, not subjected to amidation or not esterified, respectively, being salified with organic and/or inorganic bases.

* * * * *